(12) United States Patent
Noda

(10) Patent No.: US 10,550,053 B2
(45) Date of Patent: Feb. 4, 2020

(54) METHOD FOR RECOVERING OLEFIN

(71) Applicant: NGK Insulators, Ltd., Nagoya (JP)

(72) Inventor: Kenichi Noda, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 26 days.

(21) Appl. No.: 14/605,051

(22) Filed: Jan. 26, 2015

(65) Prior Publication Data
US 2015/0141729 A1 May 21, 2015

Related U.S. Application Data

(63) Continuation of application No. PCT/JP2013/073450, filed on Aug. 30, 2013.

(30) Foreign Application Priority Data

Aug. 31, 2012 (JP) .................. 2012-191953

(51) Int. Cl.
C07C 7/144 (2006.01)
B01D 53/22 (2006.01)
B01D 71/02 (2006.01)

(52) U.S. Cl.
CPC ............ C07C 7/144 (2013.01); B01D 53/228 (2013.01); B01D 71/021 (2013.01); B01D 71/024 (2013.01); B01D 2257/702 (2013.01)

(58) Field of Classification Search
None
See application file for complete search history.

(56) References Cited

U.S. PATENT DOCUMENTS

| | | | |
|---|---|---|---|
| 5,057,641 A | 10/1991 | Valus et al. | |
| 5,131,928 A | 7/1992 | Blackman et al. | |
| 6,518,476 B1* | 2/2003 | Culp | C07C 2/84 585/655 |
| 2002/0005118 A1 | 1/2002 | Cho et al. | |

(Continued)

FOREIGN PATENT DOCUMENTS

| | | |
|---|---|---|
| JP | 62-234523 A1 | 10/1987 |
| JP | 06-091130 A1 | 4/1994 |

(Continued)

OTHER PUBLICATIONS

Extended European Search Report (Application No. 33832831.5) dated Mar. 7, 2016.

(Continued)

*Primary Examiner* — Tam M Nguyen
(74) *Attorney, Agent, or Firm* — Burr & Brown, PLLC

(57) ABSTRACT

A method for recovering olefin includes: an olefin concentrating process of supplying a part or all of an olefin-containing gas containing olefin to an olefin-containing-gas separating unit that includes a separation membrane and causing this olefin-containing gas to transmit the separation membrane so as to obtain an olefin concentrated gas reduced in concentration of a component other than olefin to 1/10 or less compared with a concentration of a component other than olefin in the olefin-containing gas; and a residual-gas combustion process of disposal of residual gas that does not transmit the separation membrane in the olefin concentrating process by burning.

14 Claims, 3 Drawing Sheets

(56) References Cited

U.S. PATENT DOCUMENTS

| | | | | |
|---|---|---|---|---|
| 2003/0173085 | A1* | 9/2003 | Vinegar | E21B 43/006 166/302 |
| 2004/0191522 | A1* | 9/2004 | Haring | B01D 67/0027 428/411.1 |
| 2005/0124840 | A1* | 6/2005 | Chen | C07C 5/48 585/658 |
| 2006/0266213 | A1 | 11/2006 | Riu et al. | |
| 2007/0012189 | A1 | 1/2007 | Kang et al. | |
| 2010/0133171 | A1* | 6/2010 | Liu | B01D 67/0079 210/500.28 |
| 2010/0133187 | A1* | 6/2010 | Liu | B01D 53/228 210/640 |
| 2013/0011753 | A1* | 1/2013 | Noda | H01M 12/06 429/405 |
| 2014/0378721 | A1 | 12/2014 | Kuwana et al. | |
| 2015/0321141 | A1* | 11/2015 | Tang | B01D 71/022 96/6 |

FOREIGN PATENT DOCUMENTS

| | | |
|---|---|---|
| JP | 2007-021473 A1 | 2/2007 |
| JP | 2013159576 | 8/2013 |

OTHER PUBLICATIONS

English translation of Written Opinion (PCT/ISA/237) (PCT/JP2013/073450) dated Oct. 15, 2013.

K.A. Stoitsas, et al., "Porous Ceramic Membranes for Propane-Propylene Separation via the π-Complexion Mechanism: Unsupported Systems," Microporous and Mesoporous Materials, vol. 78 (2005), pp. 235-243.

Y.S. Lin, et al., "Cuprous-Chloride-Modified Nanoporous Alumina Membranes for Ethylene-Ethane Separation," Industrial Engineering Chemistry Research, vol. 38 (1999), pp. 2292-2298.

Fee Pitsch, et al., "An Adaptive Self-Healing Ionic Liquid Nanocomposite Membrane for Olefin-Paraffin Separations," Advanced Materials, vol. 24, No. 31, Aug. 2, 2012, pp. 4306-4310.

International Search Report and Written Opinion (Application No. PCT/JP2013/072450) dated Oct. 15, 2013.

Japanese Office Action (and translation provided by foreign counsel) for corresponding Japanese Patent Application No. 2014-533139 dated Apr. 25, 2017, 7 pages.

Caili Su, et al, "Facilitated Transport of $C_2H_4$ in a $SiO_2$-poly(n-vinylpyrrolidone)-$Ag^+$ Inorganic-Organic Hybrid Membrane," Journal of Sol-Gel Science and Technology, vol. 33, No. 3, Mar. 1, 2005, pp. 327-333.

European Office Action (Application No. 13832831.5) dated Jul. 21, 2017.

Japanese Office Action (Application No. 2014-533139) dated Aug. 22, 2017.

European Office Action (Application No. 13832831.5) dated May 30, 2018.

* cited by examiner

METHOD FOR RECOVERING OLEFIN

BACKGROUND OF THE INVENTION

1. Field of the Invention

The present invention relates to a method for recovering olefin. More specifically, the present invention relates to a method for recovering olefin that allows continuously recovering high concentration olefin from olefin-containing gas containing olefin.

2. Description of Related Art

Heretofore, for synthesis of hydrocarbon-based polymer such as polyethylene and polypropylene, the raw materials containing olefin such as ethylene and propylene are used. In this synthesis, unreacted raw materials remain in the reaction system after the end of a synthesis reaction. Accordingly, it is attempted to recover this unreacted raw materials after the end of the synthesis reaction and reuse the recovered unreacted raw materials.

For example, Patent Document 1 discloses a gas separation method for separating hydrocarbon compound using a polymer composite membrane that is composed of a porous thin membrane made of polyolefin and filled pores in the porous thin membrane with organopolysiloxane. Patent Document 2 discloses a method for the selective separation of at least one component of a feed gas stream. The method includes passing the feed gas stream containing the component through a separation unit. The method described in Patent Document 2 employs a porous membrane that has a pore diameter of from about 10 to 200 Angstroms and where a promoter liquid containing a carrier dissolved in a suitable solvent is disposed in the pores of the porous membrane. Non-Patent Document 1 discloses a separation membrane containing silver as a separation membrane for separating gas.

CITATION LIST

Patent Documents

Patent Document 1: JP-A-62-234523
Patent Document 2: JP-A-6-91130

Non-Patent Documents

Non-Patent Document 1: Microporous and Mesoporous Materials, 78 (2005) 235-243.

SUMMARY OF THE INVENTION

Problem to be Solved by the Invention

Since the methods described in Patent Documents 1 and 2 have various problems such as the cost for recovering the unreacted raw materials containing olefin, there has been a limitation on the recovered amount. For example, the methods in Patent Documents 1 and 2 have had the problem where the recoverable amount of the unreacted raw material is not worth the recovery cost. Accordingly, in practice, the recovery of the unreacted raw material using the methods in above-described Patent Documents 1 and 2 is rarely performed. For the unrecoverable raw material, the process such as combustion has been taken.

More specifically, the gas separation method described in Patent Document 1 employs the polymer composite membrane in which pores are filled with organopolysiloxane. However, this polymer composite membrane has the problem that the polymer composite cannot selectively transmit olefin alone.

The method described in Patent Document 2 employs a facilitated transport membrane. However, in the case where this facilitated transport membrane is used, there has been the problem where an extra mechanism for trapping liquid is required at the subsequent stage and thus the recovery cost is increased.

Although there are proposed various separation membranes for separating a specific component from mixed gas, for example, an organic polymer membrane doped with metal has had the problem where the selectivity is reduced in a short time for the gas at high olefin concentration. That is, the separation membrane described in Non-Patent Document 1 has had extremely low durability in the gas at high olefin concentration. The conventionally-known inorganic membrane doped with metal has low selectivity for olefin, and it has been extremely difficult to recover the high concentration olefin.

The present invention provides a method for recovering olefin that allows continuously recovering high concentration olefin from olefin-containing gas containing olefin.

Means for Solving the Problem

According to the present invention, the following methods for recovering olefin are provided.

According to a first aspect of the present invention, a method for recovering olefin includes: an olefin concentrating process of supplying a part or all of an olefin-containing gas containing olefin to an olefin-containing-gas separating unit that includes a separation membrane and causing the olefin-containing gas to transmit the separation membrane is provided, so as to obtain an olefin concentrated gas reduced in concentration of a component other than olefin to 1/10 or less compared with a concentration of a component other than olefin in the olefin-containing gas; and a residual-gas combustion process of disposal of residual gas that does not transmit the separation membrane in the olefin concentrating process by burning.

According to a second aspect of the present invention, the method for recovering olefin according to the first aspect described above further includes an olefin pressurizing process of pressurizing the olefin concentrated gas.

According to a third aspect of the present invention, in the method for recovering olefin according to the first or second aspects described above, the concentration of the component other than olefin in the olefin concentrated gas becomes 1/60 or more and 1/10 or less compared with the concentration of the component other than olefin in the olefin-containing gas.

According to a fourth aspect of the present invention, in the method for recovering olefin according to any of the first to third aspects described above, the concentration of the component other than olefin in the olefin concentrated gas becomes 1/30 or more and 1/10 or less compared with the olefin-containing gas in the olefin-containing gas.

According to a fifth aspect of the present invention, in the method for recovering olefin according to any of the first to fourth aspects described above, a concentration of olefin contained in the olefin-containing gas is 60 mol % or more.

According to a sixth aspect of the present invention, in the method for recovering olefin according to any of the first to fifth aspects described above, a concentration of olefin contained in the olefin-containing gas is 75 mol % or more.

According to a seventh aspect of the present invention, in the method for recovering olefin according to any of the first to sixth aspects described above, a concentration of olefin contained in the olefin-containing gas is 90 mol % or more.

According to an eighth aspect of the present invention, in the method for recovering olefin according to any of the first to seventh aspects described above, a pressure of the olefin-containing gas supplied to the olefin-containing-gas separating unit is 1.5 MPa or more and 2.0 MPa or less.

According to a ninth aspect of the present invention, in the method for recovering olefin according to any of the First to eighth aspects described above, the separation membrane is a membrane that at least includes: an inorganic framework containing at least one of components selected from the group consisting of carbon, silica, titania, alumina, and zirconia; and a metallic element that is dispersed in the inorganic framework and has olefin selectivity.

According to a tenth aspect of the present invention, in the method for recovering olefin according to the ninth aspect described above, the metallic element with olefin selectivity is at least one of silver and copper.

According to an eleventh aspect of the present invention, in the method for recovering olefin according to the ninth or tenth aspects described above, a ratio (A/B) between: a standard deviation [A] of concentration of the metallic element; and an average value [B] of concentration of the metallic element, in the separation membrane is equal to or less than 0.7.

According to a twelfth aspect of the present invention, in the method for recovering olefin according to any of the ninth to eleventh aspects described above, a ratio (A/B) between: a standard deviation [A] of concentration of the metallic element; and an average value [B] of concentration of the metallic element, in the separation membrane is equal to or less than 0.5.

According to a thirteenth aspect of the present invention, in the method for recovering olefin according to any of first to twelfth aspects described above, olefin selectivity of the separation membrane is equal to or more than 100.

Effect of the Invention

The method for recovering olefin of the present invention includes the olefin concentrating process of supplying a part or all of the olefin-containing gas containing olefin to the olefin-containing-gas separating unit that includes the separation membrane so as to obtain the olefin concentrated gas. This olefin concentrating process allows obtaining the olefin concentrated gas in which the concentration of the component other than olefin is reduced to 1/10 or less compared with the concentration of the component other than olefin in the olefin-containing gas. Specifically, in the olefin concentrating process, a part or all of the olefin-containing gas is supplied to the olefin-containing-gas separating unit, which includes the separation membrane. Then, the olefin concentrated gas is obtained by causing the olefin-containing gas supplied to the olefin-containing-gas separating unit to transmit the separation membrane in the olefin-containing-gas separating unit. The method thus configured for recovering olefin of the present invention allows properly recovering olefin also from the olefin-containing gas, which is conventionally disposed of by burning. For example, in the reaction performed using a raw material containing olefin, unreacted olefin can be properly recovered from the olefin-containing gas that is disposed of after the reaction. Here, the method for recovering olefin of the present invention can be used in combination with the existing olefin separation method such as distillation.

In the method for recovering olefin of the present invention, the above-described separation membrane is preferred to employ the following membrane. That is, the separation membrane is the membrane that at least includes: the inorganic framework containing at least one of the components selected from the group consisting of carbon, silica, titania, alumina, and zirconia; and the metallic element that is dispersed in the inorganic framework and has the olefin selectivity. Using this separation membrane allows recovering olefin even from the gas at high olefin concentration. Here, conventionally, it has been extremely difficult to achieve selective recovery of olefin from the gas at high olefin concentration due to the following two reasons. As the first reason, since the conventional recovery of olefin costs money, the recoverable amount of olefin is not worth the recovery cost. Accordingly, for the gas containing olefin, the process of combustion has been taken. As the second reason, in the conventional separation membrane, since there is no separation membrane that has both durability against the gas at high olefin concentration and selectivity of olefin, it has been impossible to recover olefin by the separation membrane.

DETAILED DESCRIPTION OF THE INVENTION

Hereinafter, embodiments of the present invention will be described with reference to the drawings. The present invention is not limited to the following embodiments, and changes, modifications, and improvements can be added to the embodiments without departing from the gist of the invention.

Figure 1:
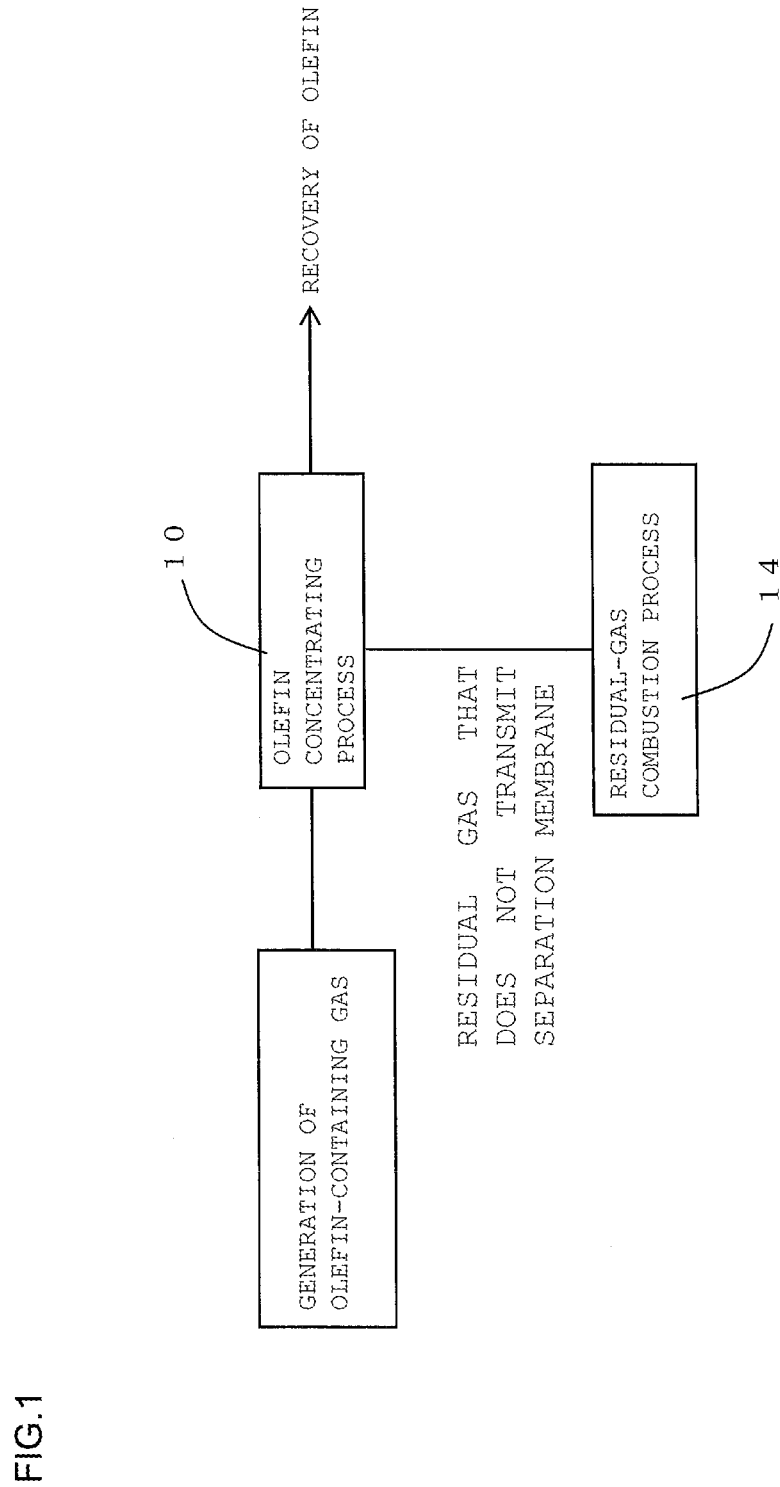
FIG. 1 is a process diagram for describing one embodiment of a method for recovering olefin of the present invention.
Figure 2:
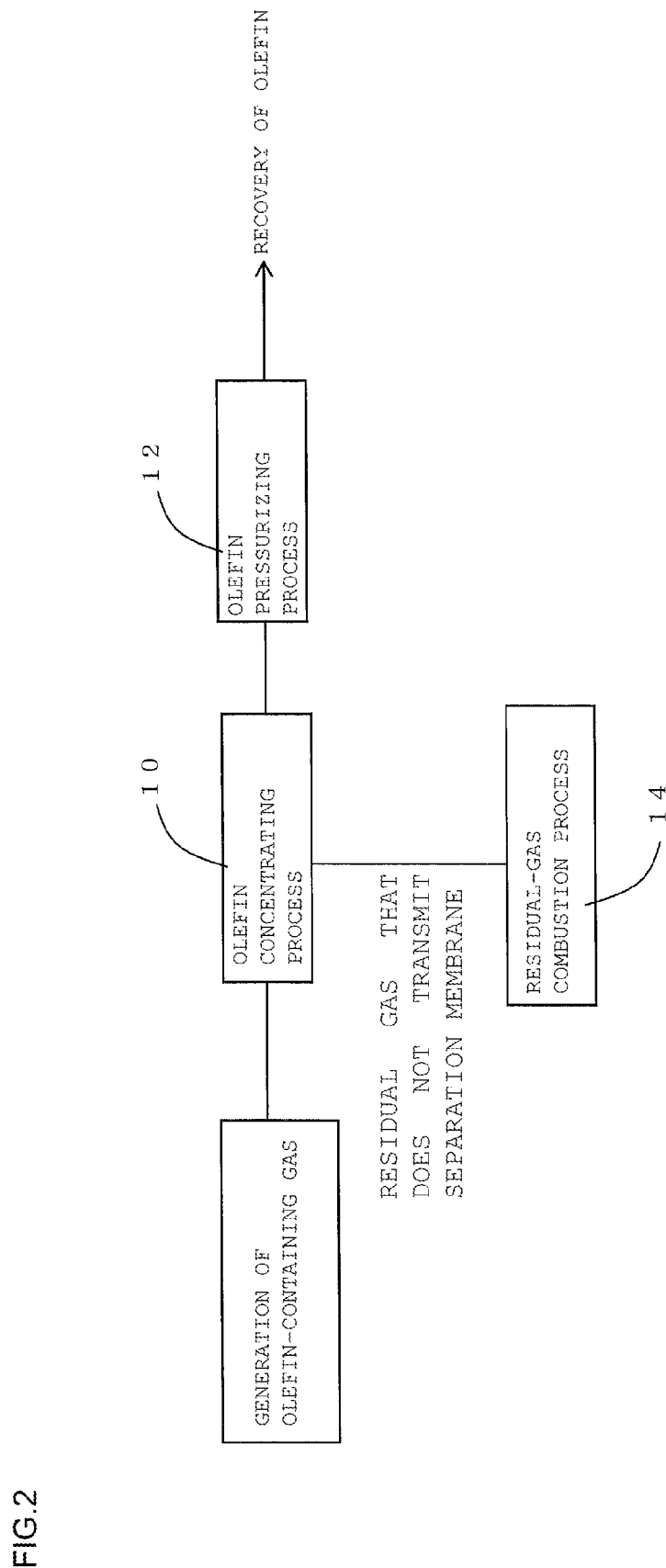
FIG. 2 is a process diagram for describing another embodiment of the method for recovering olefin of the present invention.

(1) Method for Recovering Olefin:

The method for recovering olefin of the present invention is a method for recovering olefin from olefin-containing gas containing olefin. Here, FIG. 1 is a process diagram for describing one embodiment of the method for recovering olefin of the present invention. FIG. 2 is a process diagram for describing another embodiment of the method for recovering olefin of the present invention.

Figure 3:
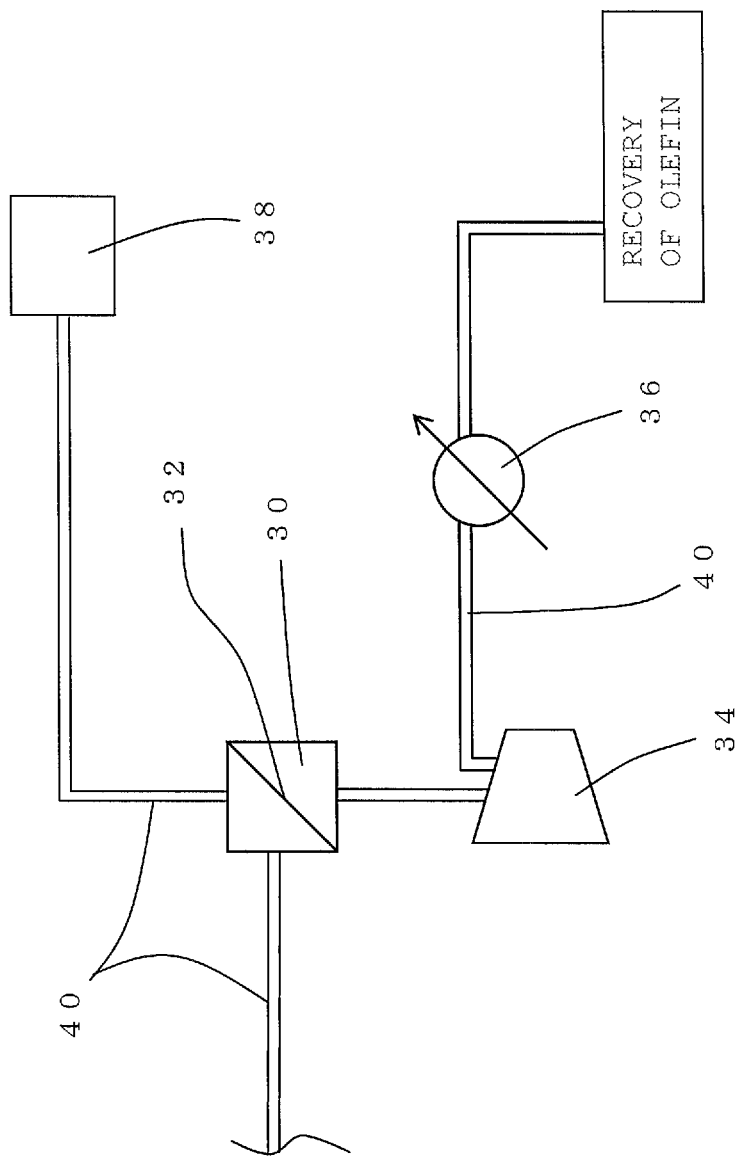
FIG. 3 is a schematic diagram showing the configuration of a recovery device used for the other embodiment of the method for recovering olefin of the present invention.

As shown in FIG. 1, the method for recovering olefin according to one embodiment of the present invention includes an olefin concentrating process 10 and a residual-gas combustion process 14. As shown in FIG. 2, the method for recovering olefin according to another embodiment of the present invention includes the olefin concentrating process 10, an olefin pressurizing process 12, and the residual-gas combustion process 14. In the olefin concentrating process, firstly, as shown in FIG. 3, a part or all of olefin-containing gas containing olefin is supplied to an olefin-containing-gas separating unit 30 that includes a separation membrane. Subsequently, this olefin-containing gas supplied to the olefin-containing-gas separating unit 30 is caused to transmit a separation membrane 32 in the olefin-containing-gas separating unit 30. This transmission through the separation membrane 32 results in obtaining olefin concentrated gas where the concentration of the component other than olefin is reduced to 1/10 or less compared with the concentration of the component other than olefin in the olefin-containing gas. Here, FIG. 3 is a schematic diagram showing the configuration of a recovery device used for the embodiment shown in FIG. 2. In a recovery device 100 shown in FIG. 3, the olefin-containing-gas separating unit 30, a compressor 34, a cooler 36, and a burner 38 are coupled together via gas piping 40.

The residual-gas combustion process is a process that disposes of the residual gas that does not transmit the separation membrane in the olefin concentrating process by burning.

The olefin pressurizing process is a process that pressurizes the olefin concentrated gas obtained in the olefin concentrating process.

In the method for recovering olefin of this embodiment, the separation membrane in the olefin-containing-gas separating unit in the olefin concentrating process is preferred to employ the following membrane. That is, the separation membrane is a membrane that at least includes: an inorganic framework containing at least one of components selected from the group consisting of carbon, silica, titania, alumina, and zirconia; and a metallic element that is dispersed in the inorganic framework and has olefin selectivity. Using this separation membrane allows continuously recovering high concentration olefin even from the gas at high olefin concentration, which cannot be recovered and is disposed of by burning up to the present.

With the method for recovering olefin according to this embodiment, olefin can be properly recovered from the olefin-containing gas, which is conventionally disposed of by burning. For example, in the reaction using a raw material containing olefin, unreacted olefin can be properly recovered from olefin-containing gas that is disposed of after the reaction.

With the method for recovering olefin according to this embodiment, the metallic element with olefin selectivity contained in the above-described separation membrane is preferred to be at least one of silver and copper, and is more preferred to be silver. Using the separation membrane containing this metallic element allows properly obtaining the olefin concentrated gas where the concentration of the component other than olefin is reduced to 1/10 or less compared with the concentration of the component other than olefin in the olefin-containing gas.

The method for recovering olefin according to this embodiment will be described further in detail below for each process described above.

(1-1) Olefin Concentrating Process:

The olefin concentrating process is the process for obtaining the olefin concentrated gas, where the concentration of the component other than olefin is reduced to 1/10 or less compared with the concentration of the component other than olefin in the olefin-containing gas, from a part or all of the olefin-containing gas containing olefin. Here, the "olefin-containing gas containing olefin" may be, for example, an olefin-containing gas generated during synthesis of hydrocarbon-based polymer such as polyethylene and polypropylene. In the above-described synthesis, a raw material gas containing olefin such as ethylene and propylene is used as the raw material. When the synthesis ends, a part of the raw material gas remains in the reaction system in an unreacted state. The residual gas containing this unreacted raw material gas has a higher concentration of the component other than olefin compared with the raw material gas. Accordingly, conventionally, although a part of olefin in the residual gas is recovered, the treatment of combustion has been taken for most of the gas as olefin-containing gas. In the method for recovering olefin according to this embodiment, this gas (that is, the above-described olefin-containing gas), which has been conventionally disposed of by burning, is used as a recovery target gas of olefin.

The concentration of the component other than olefin in the olefin concentrated gas is preferred to be 1/10 or less compared with the concentration of the component other than olefin in the olefin-containing gas, more preferred to be 1/60 or more and 1/10 or less, and particularly preferred to be 1/30 or more and 1/10 or less. In the case where the concentration of the component other than olefin in the olefin concentrated gas is larger than 1/10 of the concentration of the component other than olefin in the olefin-containing gas, the purity of the recovered olefin is insufficient. In the case where the concentration of the component other than olefin in the olefin concentrated gas is smaller than 1/60 of the concentration of the component other than olefin in the olefin-containing gas, the membrane cost might be increased due to necessity of high olefin selectivity for the separation membrane. Here, in the present invention, the "concentration" of a predetermined component in a gas means "mol concentration" of the predetermined component unless otherwise noted.

The olefin concentrated gas can be obtained by supplying the above-described olefin-containing gas to the olefin-containing-gas separating unit, which includes the separation membrane, and causing the olefin-containing gas to transmit the separation membrane in this olefin-containing-gas separating unit. As described above, this separation membrane is preferred to be the membrane that at least includes: the inorganic framework containing at least one of the components selected from the group consisting of carbon, silica, titania, alumina, and zirconia; and the metallic element that is dispersed in the inorganic framework and has the olefin selectivity.

The conventionally-known inorganic membrane doped with the metallic element with olefin selectivity has had the problem where the selectivity of olefin is low (see Non-Patent Document 1). This is estimated because the dispersivity of the metallic element is insufficient. While the detailed reason is unknown, using the raw material for membrane formation obtained by the following method when the separation membrane is prepared results in obtaining the separation membrane with high olefin selectivity. Specifically, firstly, the raw material of the inorganic framework and the raw material of the metallic element with olefin selectivity are dissolved or dispersed in a solvent. Subsequently, the solvent is stirred and mixed for 48 hours or more, more preferably for 72 hours or more at room temperature, so as to obtain the membrane formation raw material. Then, the obtained raw material for membrane formation is used to obtain the separation membrane. Using the separation membrane thus obtained in the method for recovering olefin according to this embodiment allows properly obtaining the olefin concentrated gas where the concentration of the component other than olefin is reduced to 1/10 or less in the olefin concentrating process. The separation membrane thus obtained can keep high olefin selectivity even though the concentration of olefin contained in the olefin-containing gas is high.

The dispersivity of the metallic element in the separation membrane can be evaluated by energy dispersive X-ray spectrometry (EDS). The evaluation method for the dispersivity of the metallic element in the separation membrane is as follows. Firstly, at a magnification of 2000 times, the concentration of the metallic element is measured at ten points on the surface of the separation membrane at intervals of 100 μm by EDS. From the measured concentration of the metallic element, a standard deviation [A] of the concentration of the metallic element and an average value [B] of the concentration of the metallic element are obtained, so as to obtain the ratio (that is, A/B) of the standard deviation [A] of the concentration of the metallic element to the average value [B] of the concentration of the metallic element. The value of this "A/B" allows evaluating the dispersivity of the metallic element in the separation membrane. As the separation membrane, the A/B is preferred to be 0.7 or less, and more preferred to be 0.5 or less. In the case where the A/B exceeds 0.7, the olefin selectivity of the separation membrane might be low.

The olefin selectivity of the separation membrane is preferred to be 100 or more, more preferred to be 300 or more, and particularly preferred to be 500 or more. Here, the "olefin selectivity of the separation membrane" means (the permeance of olefin)/(the permeance of the gas other than olefin). Here, the permeance means the amount of gas that transmits the membrane per unit area, unit time, and unit pressure (partial pressure) difference, and is expressed by [mol/($m^2 \cdot s \cdot kPa$)]. In the case where the olefin selectivity of the separation membrane is less than 100, there is the possibility that the concentration of the component other than olefin cannot be reduced to 1/10 or less when an appropriate amount of olefin is recovered using the separation membrane.

The separation membrane is preferred to be disposed on the surface of a porous substrate. Disposing the separation membrane on the surface of the porous substrate allows reinforcing the strength of the separation membrane. Since multiple pores penetrate the porous substrate, fluid can pass through the porous substrate.

The porous substrate that can be used for the separation membrane is preferred to employ the substrate made of: porous ceramic mainly containing at least one of alumina, titania, silica, cordierite, zirconia, mullite, and the like; or porous metal mainly containing at least one of stainless steel, nickel, and the like. In the case where the porous ceramic or the porous metal described here is the main component, the porous substrate is excellent in pressure resistance, chemical resistance, impact resistance, and the like.

For the porous substrate, from a standpoint of increasing the permeation flux of the material that transmits the separation membrane and the aspect of completely filling the open end of pores on the porous substrate with the separation membrane, pores with an average pore diameter of 0.001 to 5 μm are preferred to be opened on the surface of the substrate where the separation membrane is disposed. The average pore diameter on the surface of the porous substrate is set to a value that is measured with the perm-porometer or the nano-perm porometer.

In the separation membrane used for the method for recovering olefin of the present invention, the porous substrate may employ a single layer structure or may employ a multi-layer structure. The shape of the porous substrate is not specifically limited, but can employ, for example, a tube shape such as a cylindrical tube and a rectangular tube, a columnar shape such as a cylindrical column and a prismatic column, a plate shape such as a circular plate shape and a polygonal plate shape, a monolith form, and the like.

In the method for recovering olefin of this embodiment, the concentration of olefin contained in the olefin-containing gas is preferred to be 60 mol % or more, more preferred to be 75 mol % or more, further more preferred to be 90 mol % or more, and particularly preferred to be 90 to 99 mol. For example, when the concentration of olefin contained in the olefin-containing gas is less than 60 mol %, the separation membrane might require high olefin selectivity for obtaining the olefin concentrated gas with required purity. Furthermore, when the concentration of olefin contained in the olefin-containing gas is less than 60 mol %, the partial pressure of olefin is reduced and then the required number of the membranes increases. Accordingly, the membrane cost might be increased. In the case where the concentration of olefin contained in the olefin-containing gas is higher than 99 mol %, the degree of improvement in olefin concentration by reducing the concentration of the component other than olefin to 1/10 or less is small. Accordingly, the cost advantage for recovering olefin might be small.

The amount of the olefin-containing gas supplied to the olefin-containing-gas separating unit can be determined as necessary corresponding to the separation performance of the separation membrane of the olefin-containing-gas separating unit and the like. The amount of the olefin-containing gas supplied to the olefin-containing-gas separating unit is preferred to be 10 to 100 mol % of all the gas amount of the olefin-containing gas, more preferred to be 30 to 100 mol %, and particularly preferred to be 50 to 100 mol %.

The pressure of the olefin-containing gas supplied to the olefin-containing-gas separating unit is not specifically limited, but is preferred to be 1.5 MPa or more and 2.0 MPa or less. Supplying the olefin-containing gas to the olefin-containing-gas separating unit at a pressure of 1.5 MPa or more allows increasing the olefin transmission amount in the separation membrane. Thus, this configuration is preferred. Additionally, the pressure of 2.0 MPa or less facilitates supplying the olefin-containing gas in the gas state. Thus, this configuration is preferred.

The olefin concentrated gas obtained in the olefin concentrating process is the gas where the concentration of the component other than olefin is reduced to 1/10 or less compared with the concentration of the component other than olefin in the olefin-containing gas. Hereinafter, "the concentration of the component other than olefin reduced to 1/10 or less" means that, in comparison between the olefin-containing gas and the olefin concentrated gas, the component other than olefin in the olefin concentrated gas is 1/10 or less compared with the component other than olefin in the olefin-containing gas.

Here, in the olefin concentrating process, the gas that has not transmitted the separation membrane is disposed of as residual gas by burning in the "residual-gas combustion process" described later. The residual gas has a larger part of component other than olefin, which is existed in the olefin-containing gas, than the olefin-containing gas has and thus is not used for recovering olefin. An appropriate process of combustion is taken.

(1-2) Residual-Gas Combustion Process:

The residual-gas combustion process is the process for disposal of the residual gas, which has not transmitted the separation membrane, in the olefin concentrating process by burning. Here, in the conventional technique where olefin is not recovered, the "olefin-containing gas" as the recovery target gas of the method for recovering olefin in this embodiment is used for this residual-gas combustion process so as to be disposed of by burning. In the recovery device 100 shown in FIG. 3, the residual gas, which has not transmitted the separation membrane 32 in the olefin-containing-gas separating unit 30, is introduced into the burner 38 through the gas piping 40 and then disposed of by burning within this burner 38.

The method for burning the residual gas is not specifically limited. For example, flare combustion or catalyst combustion is possible.

(1-3) Olefin Pressurizing Process:

The olefin pressurizing process is the process for pressurizing the obtained olefin concentrated gas. The olefin concentrated gas can be pressurized by, for example, the compressor 34 as shown in FIG. 3. After the pressurization (compression) by the compressor 34, the pressurized gas may be cooled by the cooler 36.

The condition for pressurizing the olefin concentrated gas is not specifically limited. However, for example, the olefin concentrated gas is preferred to be pressurized up to 1 MPa and more preferred to be pressurized up to the pressure at which the olefin concentrated gas is liquefied. Pressurization up to this pressure allows volume reduction of the recovered olefin so as to be easy to transport.

EXAMPLES

The following describes the present invention based on Examples further in detail. The present invention is not limited to these Examples.

(Synthesis of Separation Membrane)

Under the conditions shown in Table 1, a membrane-forming solution was synthesized. Subsequently, the synthesized membrane-forming solution was applied over a porous alumina substrate and dried. Then, a heat treatment was performed at a predetermined temperature under nitrogen atmosphere, so as to prepare separation membranes (separation membranes A to J). Table 1 shows the raw materials of the membrane-forming solutions and their solvents, the stirring times of the membrane-forming solutions, the sintering temperatures in the heat treatment.

membranes D to F employed carboxyethylsilanetriol sodium salt, nitric acid, and silver tetrafluoroborate as the raw materials, and employed water as the solvents. The separation membrane G employed titanium tetraisopropoxide, diethanolamine, and silver tetrafluoroborate as the raw material, and employed isopropanol and water as the solvent. The separation membrane H employed tris-sec-butoxyaluminum, acetylacetone, and silver tetrafluoroborate as the raw material, and employed isopropanol and water as the solvent. The separation membrane I employed tetra-n-butoxyzirconium, acetylacetone, and silver tetrafluoroborate as the raw material, and employed isopropanol and water as the solvent. The separation membrane J employed polyimide and silver nitrate as the raw material, and employed N-methyl-2-pyrrolidone as the solvent.

With energy dispersive X-ray spectrometry (EDS), the silver concentration was analyzed at ten points on the surface of the separation membrane regarding the separation membranes A to J. Based on the measured metallic element concentrations, the standard deviation [A] of the silver concentration and the average value [B] of the silver concentration were obtained. The values of A/B are shown in Table 1.

Regarding the separation membranes A to J, the olefin selectivity was evaluated. The permeance in the case where ethylene at a pressure of 1.6 MPa transmitted the separation membrane was defined as an ethylene permeance. The permeance in the case of transmission of ethane at a pressure of 1.6 MPa was defined as an ethane permeance. The olefin selectivity was obtained as (the ethylene permeance)/(the ethane permeance). Here, the permeance is the amount of the gas that transmits the membrane per unit area, unit time, and unit pressure (partial pressure) difference. The result confirmed that the separation membranes A to J showed olefin selectivities. The olefin selectivities of the separation membranes A to F and J are shown in Table 1. In the

TABLE 1

| | Raw Material | Solvent | Stirring Time | Sintering Temperature | A/B | Olefin Selectivity |
|---|---|---|---|---|---|---|
| Separation Membrane A | Phenolic Resin | N-Methyl-2-Pyrrolidone | 72 Hours | 700° C. | 0.52 | 111 |
| Separation Membrane B | Silver Nitrate | | 48 Hours | | 0.60 | 105 |
| Separation Membrane C | | | 24 Hours | | 0.82 | 70 |
| Separation Membrane D | Carboxyethylsilanetriol Sodium | Water | 72 Hours | 150° C. | 0.29 | 520 |
| Separation Membrane E | Salt | | 48 Hours | | 0.45 | 307 |
| Separation Membrane F | Nitric Acid | | 24 Hours | | 0.76 | 93 |
| | Silver Tetrafluoroborate | | | | | |
| Separation Membrane G | Titanium Tetraisopropoxide | Isopropanol | 48 Hours | 150° C. | 0.65 | — |
| | Diethanolamine | Water | | | | |
| | Silver Tetrafluoroborate | | | | | |
| Separation Membrane H | Tris-sec-Butoxyaluminum | Isopropanol | 48 Hours | 200° C. | 0.63 | — |
| | Acetylacetone | Water | | | | |
| | Silver Tetrafluoroborate | | | | | |
| Separation Membrane I | Tetra-n-Butoxyzirconium | Isopropanol | 48 Hours | 150° C. | 0.50 | — |
| | Acetylacetone | Water | | | | |
| | Silver Tetrafluoroborate | | | | | |
| Separation Membrane J | Polyimide | N-Methyl-2-Pyrrolidone | 48 Hours | 200° C. | 0.57 | 35 |
| | Silver Nitrate | | | | | |

In the separation membranes A to J, the separation membranes A to I are inorganic membranes and the separation membrane J is an organic membrane. Here, the separation membranes A to C are carbon membranes since these membranes are carbonized by a heat treatment at 700° C. The separation membranes A to C employed phenolic resin and silver nitrate as the raw materials, and employed N-methyl-2-pyrrolidone as the solvents. The separation separation membranes G to I, the olefin selectivities were similar to those of the separation membranes A to F but the transmission amounts themselves tended to be slightly small. The result shown in Table 1 found that, in the separation membranes A to F, a longer stirring time during synthesis of the membrane-forming solution caused a smaller value of A/B and caused higher olefin selectivity.

Example 1

In Example 1, ethylene was recovered from an olefin-containing gas where the concentration of ethylene was 90 mol % and the concentration of the component other than olefin was 10 mol %. Hereinafter, the "olefin-containing gas where the concentration of ethylene is 90 mol %" is defined as an "olefin-containing gas A."

In the recovery of ethylene from the olefin-containing gas A, the separation membrane A was used as the separation membrane in the olefin-containing-gas separating unit.

The olefin-containing gas A at a pressure of 1.6 MPa was flowed into the olefin-containing-gas separating unit with the separation membrane A at a flow rate of 0.01 m$^3$/minutes. The olefin-containing gas A flowed into the olefin-containing-gas separating unit passed through the separation membrane A, so as to allow obtaining an ethylene concentrated gas (olefin concentrated gas) where the concentration of the component other than ethylene was reduced to 1/10 or less. Here, the gas that had not transmitted the separation membrane A was disposed of by burning.

Subsequently, this ethylene concentrated gas was pressurized by a compressor, so as to recover ethylene from the ethylene concentrated gas. The result of composition analysis found that the recovered ethylene had an ethylene concentration of 99.5 mol % or more. Here, the component of the concentration other than the corresponding concentration is a component other than olefin. Also after ethylene was continuously recovered for 1000 hours, the concentration of recovered ethylene was 99.5 mol % or more.

Example 2

Using the separation membrane E, ethylene was recovered from the olefin-containing gas A by a method similar to that in Example 1. The result found that the recovered ethylene had an ethylene concentration of 99.5 mol % or more. Also after ethylene was continuously recovered for 1000 hours, the concentration of recovered ethylene was 99.5 mol % or more.

Example 3

In Example 3, ethylene was recovered from an olefin-containing gas where the concentration of ethylene was 98 mol % and the concentration of the component other than olefin was 2 mol %. Hereinafter, the "olefin-containing gas where the concentration of ethylene is 98 mol %" is defined as an "olefin-containing gas B."

The olefin-containing gas B was used as a target gas for recovering ethylene, but otherwise ethylene was recovered by a method similar to that in Example 1. The result of composition analysis found that the recovered ethylene had an ethylene concentration of 99.9 mol % or more. Here, the component of the concentration other than the corresponding concentration is a component other than olefin. Also after ethylene was continuously recovered for 1000 hours, the concentration of recovered ethylene was 99.9 mol % or more.

Example 4

In Example 4, propylene was recovered from an olefin-containing gas where the concentration of propylene was 60 mol % and the concentration of the component other than olefin was 40 mol %. Hereinafter, the "olefin-containing gas where the concentration of propylene is 60 mol %" is defined as an "olefin-containing gas C."

The olefin-containing gas C at a pressure of 1.8 MPa was used as a target gas for recovering propylene, but otherwise propylene was recovered by a method similar to that in Example 1. The result of composition analysis found that the recovered propylene had a propylene concentration of 97 mol % or more. Here, the component of the concentration other than the corresponding concentration is a component other than olefin. Also after propylene was continuously recovered for 1000 hours, the concentration of recovered propylene was 97 mol % or more.

Example 5

In Example 5, propylene was recovered from an olefin-containing gas where the concentration of propylene was 95 mol % and the concentration of the component other than olefin was 5 mol %. Hereinafter, the "olefin-containing gas where the concentration of propylene is 95 mol %" is defined as an "olefin-containing gas D."

The olefin-containing gas D was used as a target gas for recovering propylene, but otherwise propylene was recovered by a method similar to that in Example 4. The result of composition analysis found that the recovered propylene had a propylene concentration of 99.7 mol % or more. Here, the component of the concentration other than the corresponding concentration is a component other than olefin. Also after propylene was continuously recovered for 1000 hours, the concentration of recovered propylene was 99.8 mol % or more.

Example 6

In Example 6, propylene was recovered from an olefin-containing gas where the concentration of propylene was 50 mol % and the concentration of the component other than olefin was 50 mol %. Hereinafter, the "olefin-containing gas where the concentration of propylene was 50 mol %" is defined as an "olefin-containing gas E."

The olefin-containing gas E was used as a target gas for recovering propylene, but otherwise propylene was recovered by a method similar to that in Example 4. The result of composition analysis found that the recovered propylene had a propylene concentration of 95 mol % or more. Here, the component of the concentration other than the corresponding concentration is a component other than olefin. Also after propylene was continuously recovered for 1000 hours, the concentration of recovered propylene was 95 mol % or more.

Comparative Example 1

A polyimide membrane doped with silver was used as the separation membrane of the olefin-containing-gas separating unit, but otherwise ethylene was recovered by a method similar to that in Example 1. The result of composition analysis found that the recovered ethylene had an ethylene concentration of 98 mol %. Here, the component of the concentration other than the corresponding concentration is a component other than olefin. However, after ethylene was continuously recovered for 100 hours, the concentration of ethylene was reduced to 95 mol %.

INDUSTRIAL APPLICABILITY

The method for recovering olefin of the present invention can be used as a method for continuously recovering high concentration olefin from an olefin-containing gas containing olefin.

DESCRIPTION OF REFERENCE NUMERALS

10: olefin concentrating process, 12: olefin pressurizing process, 14: residual gas combustion process, 30: olefin-containing-gas separating unit, 32: separation membrane, 34: compressor, 36: cooler, 38: burner, 40: gas piping, 100: recovery device

The invention claimed is:

1. A method for recovering olefin, comprising:
an olefin concentrating process of supplying a part or all of an olefin-containing gas containing olefin to an olefin-containing-gas separating unit that includes a separation membrane and causing the olefin-containing gas to transmit through the separation membrane, so as to obtain an olefin concentrated gas reduced in concentration of a component other than olefin to 1/10 or less compared with a concentration of a component other than olefin in the olefin-containing gas; and
a residual-gas combustion process of disposal of residual gas that does not transmit through the separation membrane in the olefin concentrating process by burning,
wherein the separation membrane comprises (i) an inorganic framework containing at least one component selected from the group consisting of carbon, silica, titania, alumina and zirconia, and (ii) a metallic element with olefin selectivity dispersed in the inorganic framework, wherein the metallic element is at least one of silver and copper, and
wherein olefin selectivity of the separation membrane is equal to or more than 100.

2. The method for recovering olefin according to claim 1, further comprising
an olefin pressurizing process of pressurizing the olefin concentrated gas.

3. The method for recovering olefin according to claim 1, wherein
the concentration of the component other than olefin in the olefin concentrated gas becomes 1/60 or more and 1/10 or less compared with the concentration of the component other than olefin in the olefin-containing gas.

4. The method for recovering olefin according to claim 2, wherein
the concentration of the component other than olefin in the olefin concentrated gas becomes 1/60 or more and 1/10 or less compared with the concentration of the component other than olefin in the olefin-containing gas.

5. The method for recovering olefin according to claim 1, wherein
the concentration of the component other than olefin in the olefin concentrated gas becomes 1/30 or more and 1/10 or less compared with the olefin-containing gas in the olefin-containing gas.

6. The method for recovering olefin according to claim 2, wherein
the concentration of the component other than olefin in the olefin concentrated gas becomes 1/30 or more and 1/10 or less compared with the olefin-containing gas in the olefin-containing gas.

7. The method for recovering olefin according to claim 3, wherein
the concentration of the component other than olefin in the olefin concentrated gas becomes 1/30 or more and 1/10 or less compared with the olefin-containing gas in the olefin-containing gas.

8. The method for recovering olefin according to claim 4, wherein
the concentration of the component other than olefin in the olefin concentrated gas becomes 1/30 or more and 1/10 or less compared with the olefin-containing gas in the olefin-containing gas.

9. The method for recovering olefin according to claim 1, wherein
a concentration of olefin contained in the olefin-containing gas is 60 mol % or more.

10. The method for recovering olefin according to claim 1, wherein
a concentration of olefin contained in the olefin-containing gas is 75 mol % or more.

11. The method for recovering olefin according to claim 1, wherein
a concentration of olefin contained in the olefin-containing gas is 90 mol % or more.

12. The method for recovering olefin according to claim 1,
wherein a pressure of the olefin-containing gas supplied to the olefin-containing-gas separating unit is 1.5 MPa or more and 2.0 MPa or less.

13. The method for recovering olefin according to claim 1, wherein
a ratio (A/B) between: a standard deviation [A] of concentration of the metallic element; and an average value [B] of concentration of the metallic element, in the separation membrane is equal to or less than 0.7.

14. The method for recovering olefin according to claim 1, wherein
a ratio (A/B) between: a standard deviation [A] of concentration of the metallic element; and an average value [B] of concentration of the metallic element, in the separation membrane is equal to or less than 0.5.

* * * * *